United States Patent
Dosmann et al.

(10) Patent No.: US 7,483,141 B2
(45) Date of Patent: *Jan. 27, 2009

(54) DIFFUSE REFLECTANCE READHEAD

(75) Inventors: Andrew J. Dosmann, Granger, IN (US); Mohammad A. Kheiri, Elkhart, IN (US)

(73) Assignee: Bayer HealthCare, LLC, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/981,941

(22) Filed: Nov. 1, 2007

(65) Prior Publication Data

US 2008/0062425 A1    Mar. 13, 2008

Related U.S. Application Data

(63) Continuation of application No. 10/739,227, filed on Oct. 27, 2003, now Pat. No. 7,304,743.

(60) Provisional application No. 60/421,626, filed on Oct. 29, 2002.

(51) Int. Cl.
   *G01N 21/47* (2006.01)
   *G01N 21/55* (2006.01)

(52) U.S. Cl. ............................................. 356/446

(58) Field of Classification Search .......... 356/445–446
   See application file for complete search history.

(56) References Cited

U.S. PATENT DOCUMENTS

| | | | |
|---|---|---|---|
| 3,150,264 A | * | 9/1964 | Ehlert ..................... 250/338.1 |
| 3,910,701 A | | 10/1975 | Henderson et al. |
| 4,265,545 A | | 5/1981 | Slaker |
| 4,603,976 A | | 8/1986 | Fetzer et al. |
| 4,838,697 A | | 6/1989 | Kurandt |
| 5,090,795 A | | 2/1992 | O'Meara et al. |
| 5,278,816 A | | 1/1994 | Russell |
| 5,518,689 A | | 5/1996 | Dosmann et al. |
| 5,611,999 A | | 3/1997 | Dosmann et al. |
| 5,723,282 A | | 3/1998 | Fahy et al. |

(Continued)

FOREIGN PATENT DOCUMENTS

WO    WO01/43113    6/2001

OTHER PUBLICATIONS

European Search Report dated Apr. 27, 2004, Application No. EP 03 02 4612, 3 pages.

(Continued)

*Primary Examiner*—Tarifur R. Chowdhury
*Assistant Examiner*—Isiaka O Akanbi
(74) *Attorney, Agent, or Firm*—Nixon Peabody LLP

(57) ABSTRACT

A glucose monitoring system comprising a readhead positioned a predetermined distance from a sample aperture. The readhead comprises first and second LEDs adapted to emit intersecting paths of light. A beam splitter is positioned at the intersection of the light paths. The beam splitter comprises a band pass filter for controlling the center wavelength of a resulting coaxial emitted light for illuminating a sample on the sample aperture. The readhead further comprises a detector which comprises a detector aperture and a molded lens over the detector aperture. A light-scattering section upstream of the lens comprises a plurality of steps having angles greater than 90 degrees to reduce internal stray light.

21 Claims, 4 Drawing Sheets

U.S. PATENT DOCUMENTS

| | | | |
|---|---|---|---|
| 5,790,259 | A | 8/1998 | Mizuhata et al. |
| 5,866,349 | A | 2/1999 | Lilja et al. |
| 6,043,506 | A | 3/2000 | Heffelfinger et al. |
| 6,152,942 | A | 11/2000 | Brenneman et al. |
| 6,181,417 | B1 | 1/2001 | Dosmann |
| 6,872,221 | B2 * | 3/2005 | Lytle .......................... 607/89 |
| 2004/0090615 | A1 * | 5/2004 | Dosmann et al. .............. 356/39 |

OTHER PUBLICATIONS

European Search Report dated May 21, 2008, Application No. EP 08003618.9, 6 pages.

* cited by examiner

DIFFUSE REFLECTANCE READHEAD

CROSS-REFERENCE TO RELATED APPLICATIONS

This application is a continuation of allowed U.S. patent application Ser. No. 10/739,227 filed Oct. 27, 2003, now U.S. Pat. No. 7,304,743 that claims the benefit of the U.S. Provisional Application 60/421,626,filed on Oct. 29, 2002, which are both hereby incorporated by reference in their entireties.

FIELD OF THE INVENTION

The present invention relates generally to blood monitoring devices with some embodiments related to glucose monitoring systems. Particular embodiments relate to a diffuse reflectance device for use with a glucose monitoring system.

BACKGROUND OF THE INVENTION

It is often necessary to quickly obtain a sample of blood and perform an analysis of the blood sample. One example in which there is a need for obtaining a sample of blood is in connection with a blood glucose monitoring system where a user must frequently use the system to monitor the user's blood glucose level.

Those who have irregular blood glucose concentration levels are medically required to regularly self-monitor their blood glucose concentration level. An irregular blood glucose level can be brought on by a variety of reasons including illness such as diabetes. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low—a condition known as hypoglycemia—a person can become nervous, shaky and confused. That person's judgment may become impaired and that person may eventually pass out. A person can also become very ill if his blood glucose level becomes too high—a condition known as hyperglycemia. Both conditions, hypoglycemia and hyperglycemia, are potentially life-threatening emergencies. Therefore obtaining accurate test results is highly important.

One method of monitoring a person's blood glucose level is by portable hand-held blood glucose testing devices. The portable nature of these devices enables the user to conveniently test his blood glucose level wherever the user may be. To check the blood glucose level a drop of blood is obtained from him, for example from the fingertip, using a separate lancing device. Once the requisite amount of blood is produced on the fingertip, the blood is harvested using the blood glucose-testing device. The blood is drawn inside the testing device, which then determined the concentration of glucose in the blood. The results of the test are communicated to the user by a display on the testing device. More detail concerning lancing devices is set forth in U.S. Pat. No. 6,152,942, which is commonly assigned and incorporated herein by reference in its entirety.

Drawbacks associated with optical instruments for reading calorimetric reactions include size, low signal throughput and accuracy errors which are due, in part, to mechanical alignment (or mis-alignment) sensitivity of the optical components. These problems are further compounded when the optical instruments require readings at more than one wavelength or at multiple wavelengths. Providing multiple wavelengths compound these problems because prior art devices produce light of each wavelength with a different light element such as a light emitting diode. Each of the light emitting diodes can not be linearly aligned, or identically aligned, with the sample. This results in the light from each of the light emitting diodes having a different intensity and different intensity distribution across the sample.

Many glucose-monitoring systems determine a concentration of glucose in the blood sample by measuring the diffused reflectance from a reagent. The reagent has a color change that is proportional to the concentration of glucose in the blood sample. Generally, diffused reflectance is the preferred method of reading the change in color of the reagent. Additional background concerning calorimetric testing and diffuse light reflectance is found in U.S. Pat. Nos. 5,723,284; 6,181,417B1; 5,518,689; 5,611,999, all of which are incorporated herein by reference in their entirety.

Current methods of reading diffuse reflectance use LEDs as a monochromatic source of illumination. The problem with using an LED is that a typical center wavelength tolerance of plus or minus 20 nm causes a variation in the diffused reflectance. The variation in wavelength around the center wavelength will cause the reagent color to vary around a reflectance corresponding to the center wavelength of the LED. This reflectance variation translates into an error in glucose concentration. An error in glucose concentration level can lead the user to take too much medicine or avoid taking enough medicine, thereby resulting in a potential seizure, coma, or even death. Thus obtaining accurate glucose concentration levels in a blood sample is critical.

One category of diffuse reflectance is two-wavelength diffuse reflectance. Current designs of two-wavelength diffuse reflectance readheads use coaxial sample illumination from LEDs at two different wavelengths. The coaxial illumination of the sample by the two LEDs is traditionally done with a beam splitter. Another method is to illuminate the sample with both LEDs tilted 15 degrees off the sample's normal optical axis.

One method for reducing the reflectance variation due to tolerance of the LED is to sort the LEDs according to tight center wavelength tolerances to reduce the spectral errors. Such sorting processes can increase the cost of LEDs by up to 15 times their nominal cost. A low cost alternative to reducing the spectral errors caused by LED center wavelength variation is taught herein. A method of coaxially illuminating the sample to be analyzed is also taught herein. Additional advantages concerning illumination, detection and blood monitoring, generally, will be apparent to those of ordinary skill in the art from the teachings herein.

OBJECT OF THE INVENTION

An object of the invention is to provide an improved blood monitoring system. A further object is to reduce cost of components associated with a blood monitoring device and in particular a glucose monitoring device.

An object of the invention is to provide improved accuracy and precision associated with results of monitoring systems. A further object is to provide improved results with use of coaxial illumination via two wavelengths.

Another object is to provide an improved method of controlling variation of center wavelengths of illumination.

Another object is to provide diffuse reflectance analysis using relatively narrow bandwidth illumination from typical off the shelf off-the-shelf LEDs having a typical center wavelength tolerance, where the narrow bandwidth is less than the variance of the LEDs. A further object is to control center wavelength with a LED, filter and beam splitter combination.

Another object is to provide an improvement for reducing internal stray light entering a detector active area in a diffuse reflectance detector.

Another object is to provide an improved monochromatic source of illumination.

Another object is to provide more accurate results for analysis based on light illumination and other techniques.

Another object is to provide an improved readhead for use in a diffuse reflectance system.

Other objects and advantages will be apparent to those of ordinary skill in the art from the teachings herein.

SUMMARY OF THE INVENTION

An embodiment of the invention is directed toward an illumination source. One such embodiment comprises a first monochromatic illumination source which comprises an associated illumination center-wavelength and associated illumination tolerance. A source emits rays defining an illumination path. A bandpass filter is positioned in the illumination path. The filter comprises an associated filter center-wavelength and an associated filter tolerance. For some applications, the filter tolerance is selected to be approximately equal to one-half the illumination tolerance with the filter center-wavelength selected to be approximately equal to the illumination center-wavelength minus the illumination tolerance.

A related embodiment of the invention is directed toward a readhead. One such embodiment comprises a first LED having a first center-wavelength associated therewith wherein the LED is adapted to emit a first path of light. A second LED comprising a second center-wavelength is adapted to emit a second path of light that intersects the first path of light at an intersection. The readhead further comprises a beam splitter positioned at the intersection wherein the beam splitter comprises a bandpass filter. The first LED, the second LED and the beam splitter are arranged to provide coaxial illumination in a first direction. For some applications, the bandpass filter comprises a relatively narrow bandpass as compared to a bandwidth or spectra associated with the first LED. At least a portion of the coaxial illumination is reflected off of a sample, thereby creating diffuse reflective light. The readhead further comprises a detector located to receive at least a portion of the diffused reflected light.

In some embodiments, the readhead is adapted for use in a monitoring system which is adapted to receive a sample and determine a parameter value, such as a glucose concentration level, based on analyzing the sample. In such an embodiment, a readhead may comprise a first LED having a first-wavelength and a first tolerance associated therewith. The first LED is adapted to emit a first path of light. A beam splitter comprising a bandpass filter is positioned in the first path of light. The beam splitter comprises a filter center-wavelength and a filter tolerance. A second LED is fixedly positioned relative to the first LED and the beam splitter. The second LED comprises a second center-wavelength and a second tolerance associated therewith. The second LED is adapted to emit a second path of light that intersects the beam splitter. The second LED, the beam splitter and the first LED are positioned to provide co-axial illumination of the sample by the first and second LEDs.

For some applications, the filter tolerance is selected to be less than the first tolerance associated with the first LED. The bandpass filter selected comprises a relatively narrow bandpass as compared to a bandwidth associated with the first LED.

The readhead further comprises a face defining an exit aperture through which the coaxial illumination passes. A sample aperture is spaced a predetermined distance from the face and positioned to be illuminated by the coaxial illumination. Thus, when a sample is located on the sample aperture, the sample will reflect the co-axial illumination.

A detector is positioned to receive at least a portion of the diffuse reflected coaxial illumination through a detection aperture. In some applications a lens is placed over the detection aperture to focus light onto an active area of the detector. The lens preferably comprises a plurality of steps defining one or more angles greater than 90 degrees. The steps of the lens are angled to reduce stray non-diffuse light rays reflected off the sample from reaching the detection area.

DESCRIPTION OF ILLUSTRATIVE EMBODIMENTS

Figure 1:
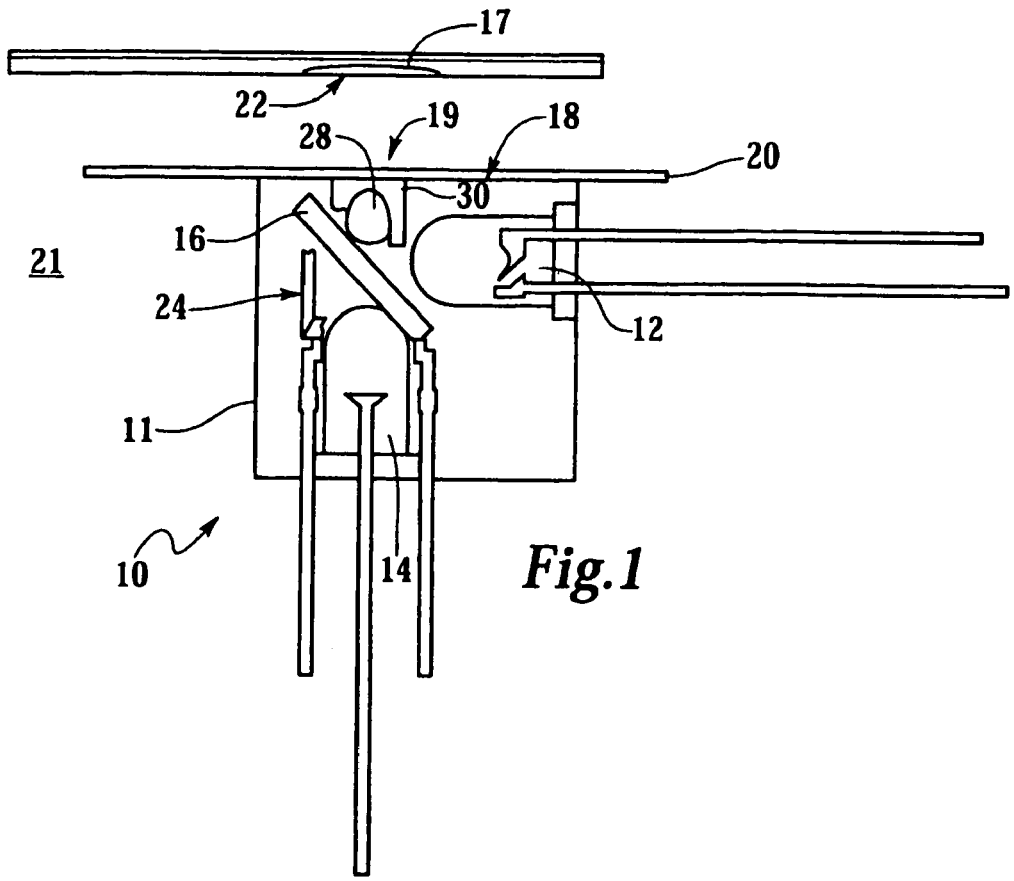
FIG. 1 shows a top view of a readhead spaced from a sample aperture.
Figure 2:
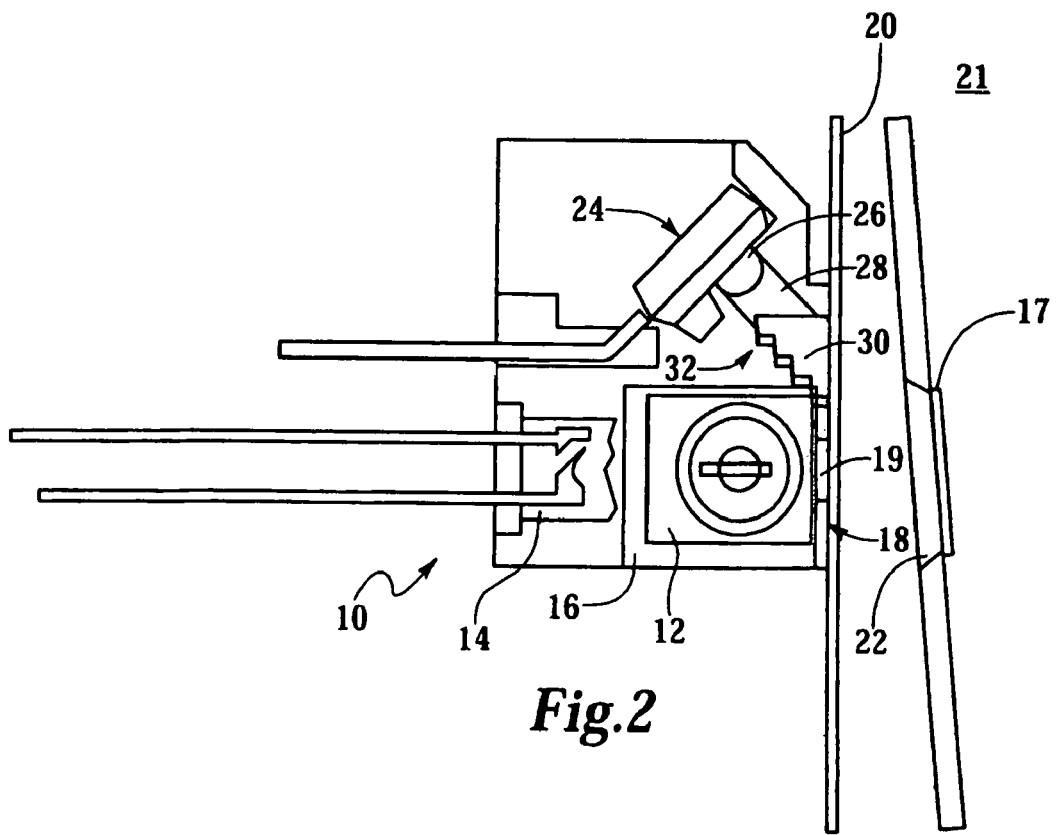
FIG. 2 shows a side view of the readhead and sample aperture shown in FIG. 1

FIGS. 1 and 2 show top and side views of a readhead 10, respectively. In particular the illustrated readhead is a 2-wavelength diffused-reflectance readhead. FIG. 1 illustrates a housing 11 supporting a first horizontal LED 12 which has a center wavelength of 940 nm. A second vertical LED 14 having a center wavelength of 700 nm is supported in the housing 11 at right angles to the first LED 12. In FIG. 2, part of the second LED 14 is cut away for clarity. One of ordinary skill in the art will understand that teachings disclosed herein are not limited to specific wavelength or sizes of LEDs. A dichroic beam splitter 16 is arranged relative to the first LED 12 and the second LED 14 to provide coaxial illumination of a sample 17 by both LEDs.

A face 18 defines an exit aperture 19 through which the coaxial illumination passes. A 0.20 mm thick polycarbonic window 20 is located over the face 18 of the readhead 10 to prevent readhead contamination.

A monitoring system 21 comprises a sample aperture 22 tilted 5 degrees off of the normal to prevent specular sample reflections from reaching a detector 24. In FIG. 1, part of the detector 24 is cut-away to better show the beam splitter 16. In a preferred embodiment, a 4.57 mm diameter sample 17 is located over a 3.81 mm by 4.32 mm oval sample aperture 22. The sample 17 is located 3.175 mm away from the readhead 10. The exit aperture is sized to produce a 3.300 mm diameter beam at the sample.

The detector 24, in a preferred embodiment, is a TAOS LS250 monolithic detector/amplifier, which is located perpendicular to the 45 degree reflection axis. The detector 24 comprises an active area (not shown) approximately 1.50 mm squared. A portion of the diffused reflective light passes through a detection aperture 28, which is also 1.5 mm squared and is positioned at the 45 degree angle. A conventional TAOS package includes a molded lens 26 downstream of the detector aperture 28 to focus incoming light onto the active area of the detector 24. Typically the readhead housing comprises a light-scattering section 30 upstream of the detection aperture 28. The light-scattering section comprises a plurality of steps 32 formed at rear right angles.

Figure 3:
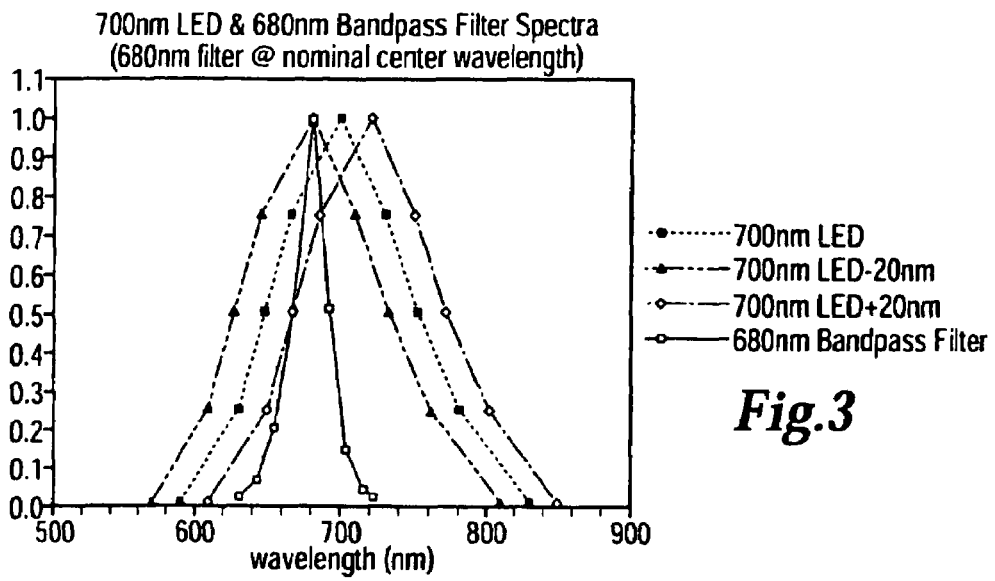
FIGS. 3-5 graphically illustrate 700 nm LED and 680 nm bandpass filter spectra.
Figure 4:
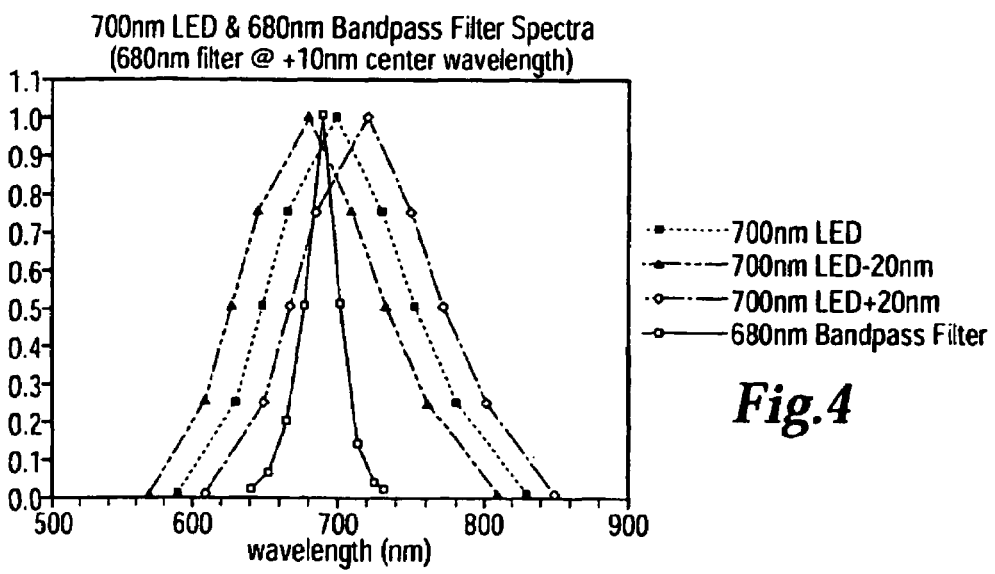
Figure 5:
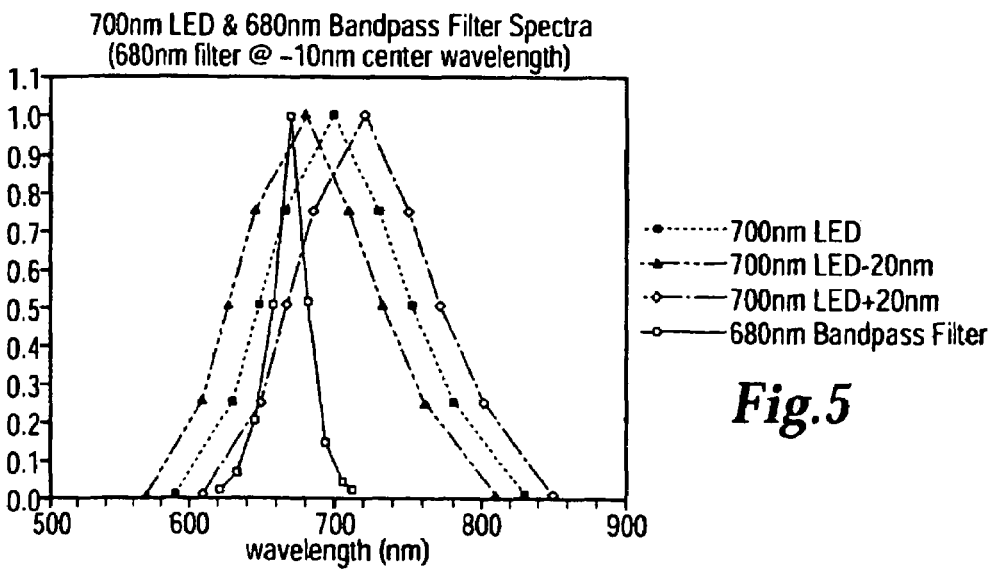

FIGS. 3, 4 and 5 depict the spectrum of the first LED comprising a 700 nm center-wavelength with a 20 nm tolerance. The first LED has a bandwidth of approximately 100 nm. Assume the same typical characteristics for the second LED, except that the center wavelength of the second LED is positioned at 940 nm. One of ordinary skill in the art will observe that the upper spectra of the first LED falls at 820 nm and the lower spectra of the second LED also falls at 820 nm. Thus even with a separation of 240 nm between center wavelengths, there is a potential overlap in the beam comprising co-axial illumination formed from the first LED and the second LED.

To prevent overlap between the rays from the first LED and the second LED, a is bandpass filter is used with the beam splitter. In a preferred embodiment, the bandpass filter is a two color filter integral with the beam splitter. The beam splitter is thereby preferably a dichroic beam splitter 16. Other beam splitter and bandpass filter combinations, in accordance with the teachings herein, will be apparent to those of ordinary skill in the art.

FIGS. 3-5 illustrate use of a 25 nm full width half-maximum bandpass filter for the beam splitter 16. The filter center wavelength is set at 680 nm. The filter tolerance used in FIGS. 3-5 is 10 nm. The center wavelength tolerance of 10 nm is commonly available at a low cost. Examining FIGS. 3-5 at the full width half maximum (FWHM) it is apparent that, with reference to FIG. 3, there are only minor variations in center wavelength characteristics of the filtered 700 nm LED light with a plus or minus 20 nm LED center wavelength shift. Similarly, FIGS. 4 and 5 show a plus or minus 20 nm variation in center wavelength of the LED spectra with the bandpass filter center wavelength of 680 nm plus or minus 10 nm.

The only condition that significantly alters the filtered center wavelength is when the LED center wavelength is at 700 nm plus 20 nm and the filter center wavelength is at 680 nm minus 10 nm. This condition forces the combined center wavelength toward a nominal 680 nm. Therefore, large center wavelength variations plus or minus 20 nm will not significantly change the spectra output of the splitter 16.

Figure 6:
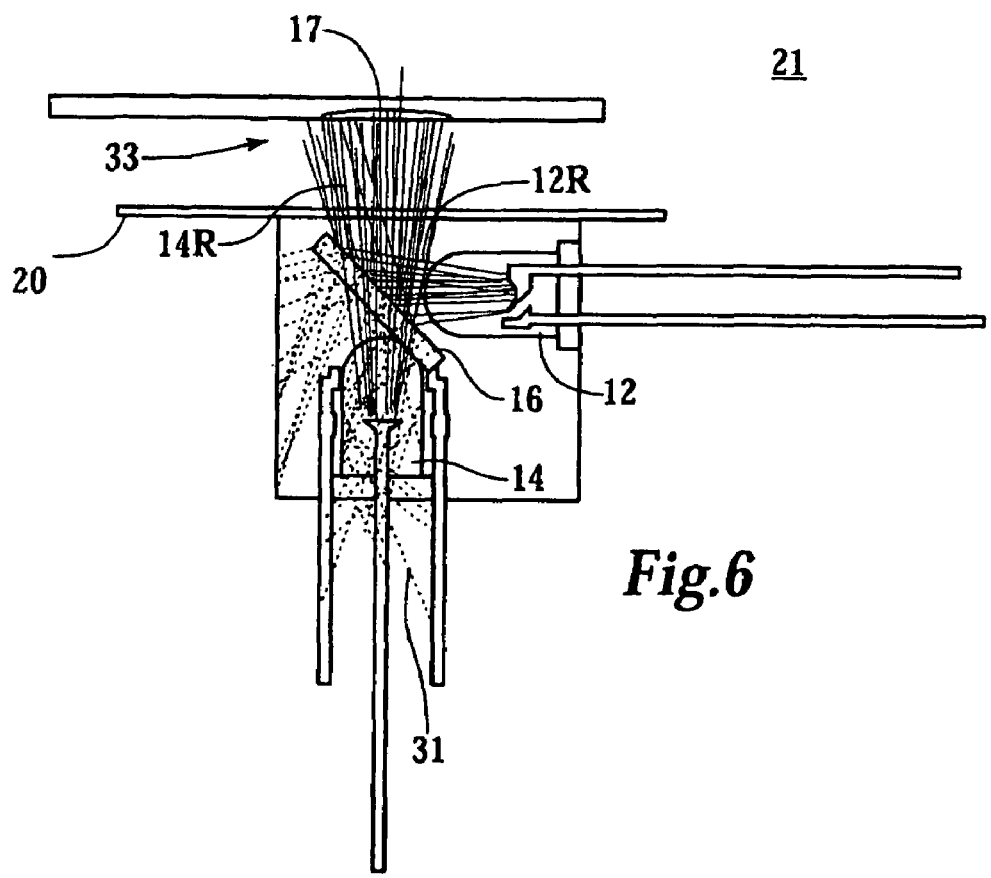
FIG. 6 shows a top view of a 700 nm LED illuminating a dichroic filter.

FIG. 6 illustrates out-of-band rays 31 blocked by the splitter 16 while in-band rays 14R are passed through the splitter 16. All of the 940 nm rays 12R associated with the second LED reflect off the bandpass filter 16 to illuminate the sample aperture 22, and thereby the sample. The two sets of rays 14R and 12R combine to illuminate the sample aperture 22. Detector 24 is removed for clarity.

Use of a combination beam splitter and bandpass filter, such as a dichroic filter, results in a significant cost savings. For example, the difference in cost between a custom 680 nm T1 LED with a specific bend width (Shinkoh Electronics Corporation, QDI KL724-680) and a 700 nm T1 LED (Lite-On Inc., LTL-4212) is approximately $4.00. A cost estimate of the dichoric filter (beam splitter) is a $1.09 (OCLI Inc.) a cost savings of approximately $3.00 could be realized with a 700 nm LED in a band pass filter combination. The cost of the TAOS detector is $1.02 (at 50 k/year). The new readhead design provides a two wavelength diffuse reflectance readhead at a low cost. Thus current components cost approximately $11.00 while the readhead according to the teachings hearing cost approximately $3.00 to $4.00

Figure 7:
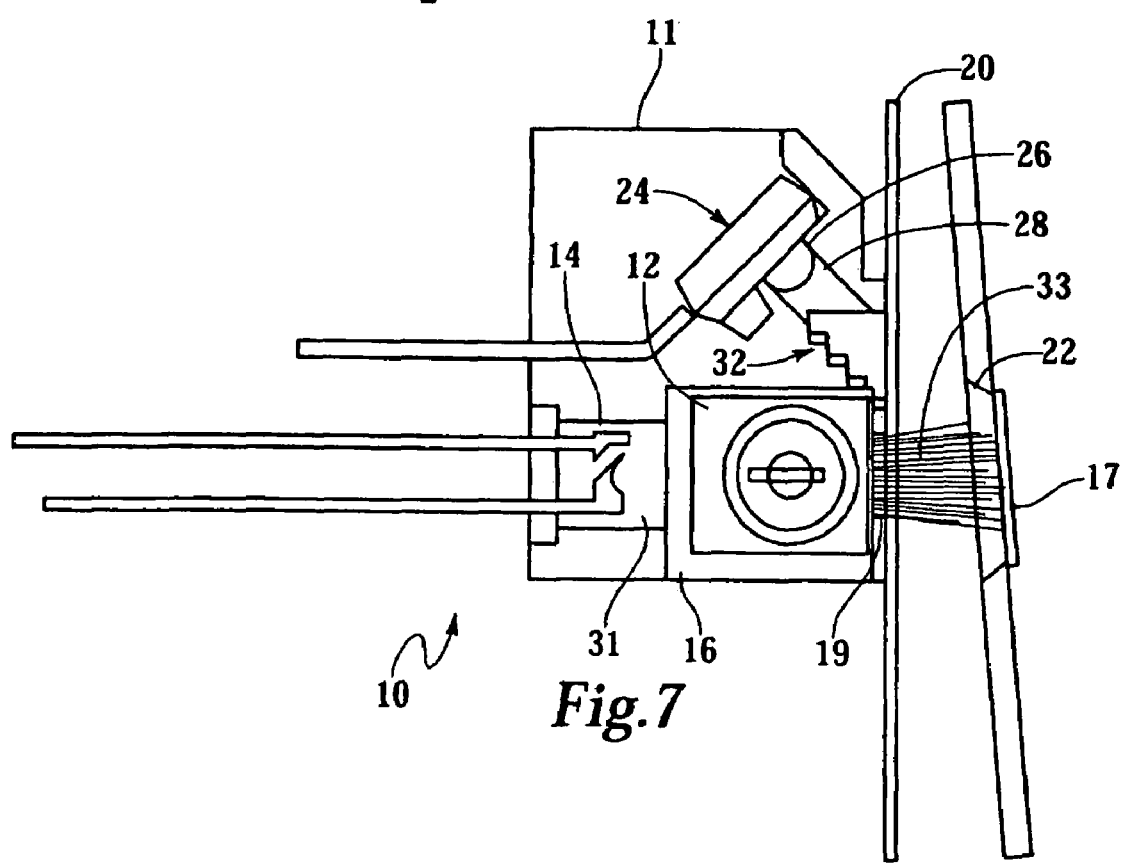
FIG. 7 shows a detector aligned with the 45 degree reflectance angle.

FIGS. 6 and 7 show the 700 nm T1 LED illuminating the dichoric 680 nm bandpass filter 16. The detector 24 is mounted at a 45 degree angle from the sample normal axis to detect a diffuse reflected light. Spectra reflections of the sample are directed away from the detector 24 active area or blocked from reaching the detector active area by steps 32 within the light-scattering section 30.

The filter 16 passes a 25 nm bandwidth of light at a center wavelength of 680 nm plus and minus 5 nm, i.e., 650 nm to 710 nm. A filtered light passes through a two millimeter diameter exit aperture 19. And the 940 nm T1 LED output reflects off of the dichroic beam splitter 16 and passes through the two millimeter diameter exit aperture 19. Together, LEDs 12 and 14 illuminate the sample with a 3.3 millimeter diameter coaxial bean 33.

Figure 8:
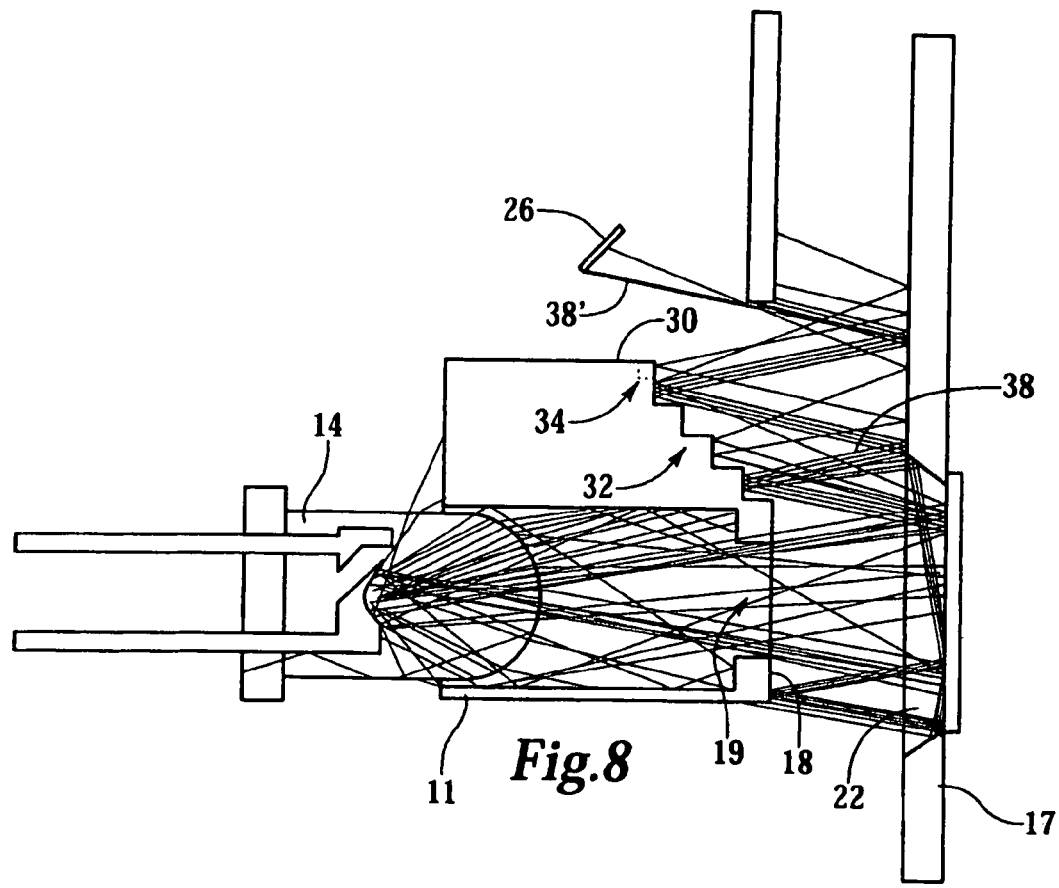
FIG. 8 shows light rays reflected from a conventional molded readhead housing having 90 degree steps.
Figure 9:
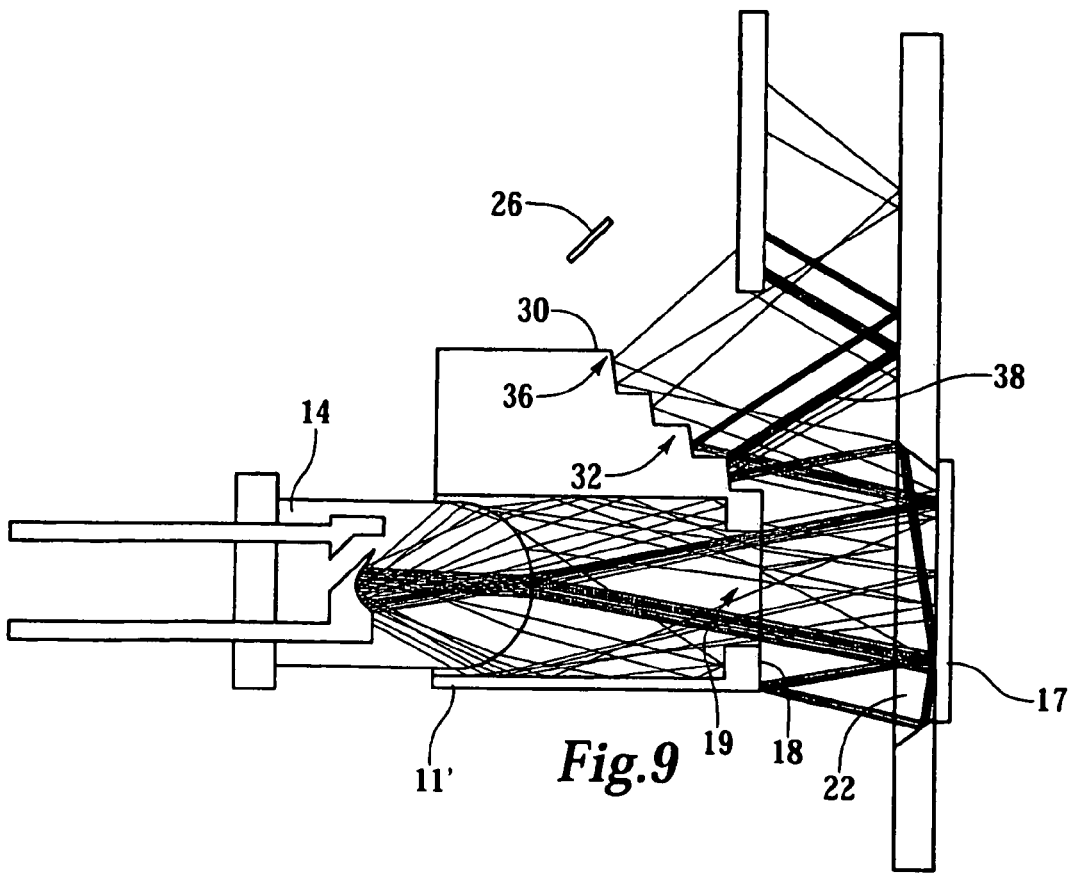
FIG. 9 shows light rays reflected from a modified molded readhead housing having 100 degree steps.

Two readhead housings (11, 11'), depicted in FIGS. 8 and 9, were modeled with light-scattering steps 32 at 90 a degree angle (ref. no. 34) and at a 100 degree angle (ref. no. 36). For simplicity, as well as to minimize test variables, one LED 14 was used; a filter and a second LED were not incorporated into the angle-step test. The steps are designed to prevent specular reflections off of the sample from reaching the detector active area 26, which reduces internal stray light (i.e., non-diffused light). The 90 degree step 34 is more likely to reflect a specular ray 38 back-up into the sample aperture 22, where the ray 38' can reflect back onto the detector active area 26, as internal stray light. A specular ray 40 reflecting off of a 100 degree step 36 is directed away from the sample aperture 22, and is less likely to reach the detector active area 26 after reflecting off of the aperture 22. In modeling, the reflectance was measured off of a mirror sample to determine internal specular light rejection. The readhead with a 90 degree step 34 hitting mirror reflectance of 0.17% R, while the 100 degree step 36 had a mirror reflectance of 0.07% R. The 100 degree step 36 design provides an improvement in internal stray light rejection.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the claimed invention, which is set forth in the following claims.

What is claimed is:

1. A readhead adapted for use in a monitoring system adapted to receive a sample on a sample aperture and determine a parameter valve based on analyzing the sample, the readhead comprising:

a first LED having a first center-wavelength associated therewith and being adapted to emit a first path of light;

a beam splitter positioned in the first path of light;

a second LED positioned relative to the first LED and the beam splitter and having a second center-wavelength associated therewith and being adapted to emit a second path of light intersecting the beam splitter, wherein the first and second paths of light interact with the beam splitter forming a beam of illumination comprising light from the first LED and the second LED;

a face defining an exit aperture through which the beam passes, wherein the sample aperture is spaced from the face and positioned to be illuminated by the beam such that when the sample is located on the sample aperture, the sample will reflect at least a portion of the beam;

a detector comprising an active area and a detection aperture positioned to receive at least a portion of diffuse light resulting from the reflected beam; and a light-scattering section positioned upstream of the detector active area, the light-scattering section including a plurality of steps defining one or more angles greater than 90 degrees and the section being positioned such that the plurality of steps are angled to reduce stray internal light on the detector active area.

2. The readhead of claim 1, wherein at least one angle defined by the plurality of steps is approximately 100 degrees.

3. The readhead of claim 1, wherein the second center-wavelength is greater than the first center-wavelength.

4. The readhead of claim 3, wherein:
the beam splitter comprises a bandpass filter having a filter center-wavelength and a filter tolerance associated therewith; and
the filter center-wavelength and filter tolerance are selected to separate wavelengths associated with the first LED from wavelengths associated with second LED such that the light in the beam from the first LED does not have wavelengths equal to wavelengths of light in the beam from the second LED.

5. The readhead of claim 3, wherein
the first LED has associated therewith a first bandwidth and a first tolerance,
the second LED has associated therewith a second bandwidth and a second tolerance, and
the beam splitter comprises a filter.

6. The readhead of claim 5, wherein the filter has associated therewith a filter center-wavelength less than approximately the second center-wavelength plus the second tolerance.

7. The readhead of claim 6, wherein the filter center-wavelength is less than approximately the first center-wavelength plus the first tolerance.

8. The readhead of claim 7, wherein the filter center-wavelength is less than approximately the first center-wavelength minus the first tolerance.

9. The readhead of claim 7, wherein the filter center-wavelength is less than approximately the first center-wavelength minus 20 nm.

10. The readhead of claim 9, wherein the filter has associated therewith a tolerance less than approximately 20 nm.

11. A glucose monitoring system comprising:
a sample aperture; and
a readhead positioned a predetermined distance from the sample aperture, the readhead comprising
a first LED and a second LED, the first and second LEDs configured to emit intersecting paths of light,
a beam splitter positioned at a point where the paths of light emitted from the first and second LEDs intersect, the beam splitter comprising a filter for controlling a center wavelength of a resulting coaxial emitted light for illuminating a sample on the sample aperture, and
a detector comprising a detector aperture and a lens positioned generally over the detection aperture, a light-scattering section of the lens comprising a plurality of steps having angles greater than 90 degrees to reduce internal stray light.

12. The system of claim 11, wherein
the first LED has associated therewith a first bandwidth and a first tolerance,
the second LED has associated therewith a second bandwidth and a second tolerance,
the filter has associated therewith a filter bandpass being relatively narrow compared to the first bandwidth and the second bandwidth.

13. The system of claim 11, wherein
the filter has a filter center-wavelength and a filter tolerance associated therewith, and
the filter center-wavelength and filter tolerance are selected to separate wavelengths associated with the first LED from wavelengths associated with second LED such that the light in the beam from the first LED does not have wavelengths equal to wavelengths of light in the beam from the second LED.

14. The system of claim 11, wherein the first LED has a first center-wavelength associated therewith and the second LED has a second center-wavelength associated therewith.

15. The system of claim 14, wherein the second center-wavelength is greater than the first center-wavelength.

16. The readhead of claim 14, wherein the filter has associated therewith a filter center-wavelength less than approximately the second center-wavelength plus a second tolerance.

17. A readhead comprising:
a first LED and a second LED, the first and second LEDs configured to emit intersecting paths of light;
a beam splitter positioned at a point where the paths of light emitted from the first and second LEDs intersect, the beam splitter comprising a bandpass filter associated therewith, the bandpass filter comprising a relatively narrow bandwidth compared to a bandwidth associated with the first LED; and
a detector comprising a detector aperture and a lens positioned generally over the detection aperture, a light-scattering section of the lens comprising a plurality of steps having angles greater than 90 degrees to reduce internal stray light.

18. The readhead of claim 17, wherein:
the bandpass filter has a filter center-wavelength and a filter tolerance associated therewith, and
the filter center-wavelength and filter tolerance are selected to separate wavelengths associated with the first LED from wavelengths associated with second LED such that the path of light emitted from the first LED does not have wavelengths equal to wavelengths of the path of light emitted from the second LED.

19. The readhead of claim 17, wherein the first LED has a first center-wavelength associated therewith and the second LED has a second center-wavelength associated therewith.

20. The readhead of claim 19, wherein the second center-wavelength is greater than the first center-wavelength.

21. The readhead of claim 19, wherein the filter has associated therewith a filter center-wavelength less than approximately the second center-wavelength plus a second tolerance.

* * * * *